(12) United States Patent
Goldstein (10) Patent No.: US 6,172,759 B1
(45) Date of Patent: Jan. 9, 2001

(54) TARGET GAS DETECTION SYSTEM WITH RAPIDLY REGENERATING OPTICALLY RESPONDING SENSORS

(75) Inventor: Mark K. Goldstein, Del Mar, CA (US)

(73) Assignee: Quantum Group Inc., San Diego, CA (US)

(*) Notice: Under 35 U.S.C. 154(b), the term of this patent shall be extended for 0 days.

(21) Appl. No.: 09/260,118

(22) Filed: Mar. 2, 1999

Related U.S. Application Data (60) Provisional application No. 60/076,822, filed on Mar. 4, 1998.

(51) Int. Cl.[7] .................................................. G01N 21/00
(52) U.S. Cl. .............................. 356/437; 422/57; 436/164
(58) Field of Search .................................. 356/437, 435; 436/134, 164, 169, 81; 422/57, 91

(56) References Cited

U.S. PATENT DOCUMENTS

| | | | |
|---|---|---|---|
| 4,043,934 | 8/1977 | Shuler et al. | 252/186 |
| 4,464,653 | 8/1984 | Winner | 340/501 |
| 5,063,164 | 11/1991 | Goldstein | 436/169 |
| 5,280,273 | 1/1994 | Goldstein | 340/632 |
| 5,302,350 | 4/1994 | Goswami et al. | 422/86 |
| 5,346,671 | 9/1994 | Goswami et al. | 422/86 |
| 5,405,583 | 4/1995 | Goswami et al. | 422/86 |
| 5,573,953 | * 11/1996 | Marnie et al. | 436/164 |
| 5,618,493 | * 4/1997 | Goldstein et al. | 536/134 |
| 5,624,848 | 4/1997 | Marnie et al. | 436/164 |

* cited by examiner

*Primary Examiner*—Hoa Q. Pham
*Assistant Examiner*—Sang H. Nguyen
(74) *Attorney, Agent, or Firm*—Christie, Parker & Hale, LLP (57) ABSTRACT

The present invention provides an apparatus and method for determining the concentration and/or hazard from a target gas by means of optically monitoring one or more sensors that responds to the target gas by means of an optical change. The apparatus comprises a photon source optically coupled to the sensor and the photon intensity passing through the sensor is quantified by more than one photodiode in a system, so that the photon flux is a function of at least one sensor's response to the target gas, e.g., transmits light through the sensor to the photodiode. The photocurrent from the photodiode is converted to a digital sensor reading value proportional to the optical characteristics of the sensors and is loaded into a microprocessor or other logic circuit. In the microprocessor, the sensor readings are essentially differentiated to determine the rate of change of the sensor readings. The rate of change information is used to trigger an alarm condition indicative of a predetermined level and or hazard of sensed toxins. In addition a preferred method to meet the BSI CO Standard is described using two sensor systems and two sensor on different sensitivity within one housing. The two separate sensor housing uses two LEDs and two photodiodes while the single housing dual sensor uses one LED and two photodiodes. The novel two sensor method to meet the BSI CO standard may not necessarily incorporate a digital display.

29 Claims, 3 Drawing Sheets

TARGET GAS DETECTION SYSTEM WITH RAPIDLY REGENERATING OPTICALLY RESPONDING SENSORS

RELATION TO COPENDING PATENT APPLICATION

This patent application is a conversion of U.S. Provisional Patent Application Serial No. 60/076,822, that was filed on Mar. 4, 1998.

FIELD OF THE INVENTION

This invention relates to detection systems used to detect harmful levels of a target gas in the air and, more particularly, relates to a target gas detection system comprising a set of optically-responding sensors that are designed to determine the concentration of a target gas by measuring sensor photon transmission levels, and be rapidly regenerating.

BACKGROUND OF THE INVENTION

The present invention relates to a sensing system comprising a set of optical responding sensors (a set consisting of at least one sensor) for detecting the presence of at least one target gas and, more particularly, to an apparatus incorporating two sensors in the sensing system, and a method for determining the concentration of at least one target gas by monitoring the optical response of the sensor within a given period of time, for use as monitoring devices in a wide variety of applications, such as home safety, occupational health, industrial, commercial, recreational and medical, and specifically to meet the British Standard Institute carbon monoxide standard.

SUMMARY OF THE INVENTION

There is provided several preferred embodiments of the present invention, i.e., an apparatus and method for determining the concentration or hazard of any particular target gas by a sensor or sensor system that changes its optical properties in response to said gas and return to the normal state after the target gas is removed very rapidly. The basic method is to measure the rates of the reactions, i.e., the forward and regeneration. A simplification of the exponential Coburn type equation into a simple differential equation so they may be easily approximated by the simpler equation (s) such as equation 1 or 2 or by means of a look up table system. These simple equation can be used in small inexpensive microprocessors or other logic circuits. A series of sensors are placed close together within a sensing system, e.g., in a row so that they may be monitored conveniently. Each of these sensors may be best used over the linear portion of its response curve (if the carbon monoxide concentration is above a certain level D) thus simplifying most of the complex equations to very simple programming to measure slope, as previously described in U.S. patent application Ser. No. 80/026,534. Then under special low carbon monoxide (CO) concentration (less than L) the most sensitive sensor response may be approximated by a simple equation or a look-up table.

EXAMPLE of a Carbon Monoxide Sensing System to meet British Standard Institute (BSI) carbon monoxide standard.

For example, a low power application of the invention includes the steps of intermittently measuring optical characteristics of an optical responding sensor or sensor system using pulsed technology, differentiating a plurality of measurements over time to obtain both the I(n) value(s) at time t and the rate of change of the measured optical characteristics of the sensors, and determining the concentration of target gas as a function of both I(n) at time t and the rate of change of the measured optical characteristics at time interval t(0) and time t. The target gas concentration information may be calculated by means of a look up table or may be calculated by an algorithm and then set to signal and or display the alarm. The simplest way to meet the BSI CO standard is to set the software to the specific requirements of that standard which included 45 ppm no response in 60 minutes, 150 ppm in 35 minutes, 350 in 6 minutes both alarm levels must reset within 15 minutes in clean air. There are temperature and humidity tests that don't present any problems for standard products that meet UL 2034. The over range test is unique, it requires 3 separate exposure over 30 day periods to 5000 ppm with reset with 30 minutes for each test.

Exemplary apparatus according to the present invention for implementing the method includes at least one and in some cases two light emitting diodes (LEDs) and two photodiodes with the target gas sensors located so that the photons pass through the sensors and the amount of light transmitted is measure by the photodiode response to that light. Each LED illuminates a corresponding sensor, and the light transmitted through the sensor is received by the photodiode.

For a low power low cost embodiment of the invention designed to determine the concentration of CO as the target gas, it is desirable to change the analog signal to digital (at very low power and low cost), the resulting photocurrent from the photodiode, proportional to the transmitted light received by the photodiode, charges a series of capacitors set to a threshold value programmed into the microprocessor as an action level such as an alarm point. The charging time of the series capacitors along with the voltage or current measured by the series of photodiodes I(n)s is recorded by the microprocessor to produce a plurality of sensor readings proportional to the darkness of the CO sensor and its rate of change. Differences of adjacent readings in the second sensor are determined only when the first sensor is saturated (no longer changing or is below a certain level such as 20% transmission. If the detector register exceeds a predetermined value or the concentration goes above a certain value, or the TWA exceed a specific value the a condition of alarm may be so indicated. And if the second sensor regenerates do to clean air it can be seen long before the first sensor regeneration can be seen. This is the key to meeting the BSI standard at 5000 ppm CO over range tests.

BRIEF DESCRIPTION OF THE DRAWINGS

The invention will be better understood with reference to the following detailed description and accompanying drawings wherein.

DETAILED DESCRIPTION

The present invention relates to an apparatus incorporating two sensors in the sensing system, and a method for determining the concentration of at least one target gas by monitoring the optical response I(n) of the sensor (S) at a time "t" and then taking derivative of the optical response with respect to time, dI/dt, and then calculating various parameters of interest such as gas concentration, Traveling Weighted Average (TWA), peak concentration over some predetermined time interval, total dose from target gas exposure, and or alarm point, warning, etc. Once the digital information is obtained from the measurement it can be-used to trigger an alarm at a predetermined value A, other warning signal, or display information. The second sensor is used to allow rapid reset from regeneration when the exposure to the first sensor causes saturation, i.e., when the first sensor darkens below a predetermined value D that can not be monitored by the first sensing system then the microprocessor switches to the second sensor. The first sensor is more sensitive than the second sensor. Thus the range of response is increased as well as the ability of the detector to reset rapidly in when the CO is removed. The field of the invention relates to gas monitoring devices for a wide variety of applications, such as home safety, occupational health, industrial, commercial, recreational and medical and specifically to meet the BSI carbon monoxide standard.

An optically responding sensor system for detecting the presence of a predetermined target gas, such as carbon monoxide ("CO"), is disclosed in U.S. Pat. No. 5,063,164 and is incorporated herein by reference. The sensor comprises at least one self-regenerating sensing reagent coated onto a substrate, for example, a high surface area transparent material. The substrate is made of a solid state material that is sufficiently transmissive or reflective to photons in the wavelength of interest to permit detecting optical characteristics of the sensor using an optically-coupled light emitting diode and photodiode collectors in a circuit designed to measure the output of the photodiode and/or its rate of change, dI/dt. Under certain conditions, the derivative is proportional to the CO concentration plus the photon intensity "I" or the change in photon light intensity delta I, "t" is time and therefore dI/dt is the rate of change of light intensity with respect to time. Therefore the carbon monoxide concentration [CO] can be represented by the following equations:

$$dI/dt + v(I) = k[CO] \quad \text{Equation 1}$$

or $$dI/dt + V(\text{delta I}) = k'[CO] \quad \text{Equation 2}$$

below some value of I or delta I v=0, then $[CO]=k_1\{dI/dt\}$, at other times $$[CO]=V\{I(n)\}+V\{\text{delta I}\}$$

When dI/dt is very near zero

Equation 1 requires a calibration point. However, Equation 2 can be designed to allow the delta above a certain amount to cause a different value to be assigned to V. There can be several delta I values which can be used to calculated the [CO] and or TWA. The approximation can be employed easily and can limit the cost of the digital alarm or detector.

Other approximations are also possible, e.g., the sum of averages or weighted averages over a series of registers. However, to meet the BSI CO standard it is necessary to reverse from 5000 ppm in less than 30 minutes. This is difficult with the S50 and S30 sensors because the optical range of the photodiode and LED can not see the very dark sensor change after the air is cleared even after 1 hour. Therefore a system that uses a second sensor with a higher threshold should be used. This switch to the second sensor can be accomplished by means of software, e.g., one adapted to reset a biomimetic sensing system in about 5 to 10 minutes with the 5K is used as the second sensor. The key is the switching from sensor 1 to sensor 2 when sensor I is saturated. Note that the sensor 1 may be a S50 sensor which may be either a single or double disk sensor and sensor 2 is a 5K sensor designed to respond slowly to 5000 ppm by the addition of more copper (about 100 to 500% more copper) to the formulation which is disclosed in U.S. Pat. No. 5,063,164.

There are several methods of monitoring the alarm point including a fixed point set by calibrating a bridge or similar circuit. On the other hand, to effect rapid regeneration it is necessary to see a rapid change in the sign of the slope. Therefore, any microprocessor-based software that can measure the sign of the slope is suitable for purposes of accomplishing such task. Another low cost method is to use some form of an analog-to-digital converter and equation 2 which can be written in the following form:

$$[CO]=k1(dI/dt)+V[\text{delta I}]$$

There are two basic optical techniques that can be incorporated as embodiments of the optical monitoring method, e.g., 1) transmission and 2) reflection. Let us first describe the transmissive method. These methods can be used for a variety of gases for which a similar responding optical sensor exists; however, as an example carbon monoxide (co) will be discussed as the target. By this exemplary focus on CO we in no way intend to limit the target gases of this method.

In the absence of CO concentration above the threshold, i.e., operating in relatively clean air, the sensor is in the normal state or condition indicated by a transmission of light (photons in the wavelength band of interest) which is indicated by a characteristic optical value I(0) and a zero value of the first and second derivatives. If a target gas such as CO is present, the sensor equilibrium is shifted as the reagent undergoes changes in its optical density, i.e., the sensor begins to Changes its optical properties, e.g., it darkens or lightens depending on the particular sensor and target gas. After a time t(0)+t(1), which depends upon the gas (such as co) concentration and the duration of exposure to the target gas such as CO, the sensor reaches a certain optical condition, e.g., darkened or lighten by a specific amount delta I(n). For the case where the sensor is at least two CO responding sensors with increasing thresholds, e.g., a series referred to as S34, S50, S100, and 5K, where the threshold of each is 15–30, 50–100, 100–150 and above 200 ppm CO, respectively.

A second embodiment of the invention employs the use of reflected photons to monitor the gas exposure and concentration of the target gas. This method is similar to the one described above except that the photons are reflect off of the sensor(s). A third embodiment of the invention combines the two methods above.

One skilled in the art would appreciate an apparatus and method for digitally tracking the response of optically responding sensors for a variety of target gases, because today current digital gas detection products can not operate for years or even monthly with common batteries such as 1.5 volt AA, AAA or 9 volts or similar batteries. Such an apparatus can be easily operated in system detector connected to a central panel by wires or RF link. Such an apparatus and method would increase the desirability of a wide variety of products from commercial, industrial and home detectors to personnel monitors, medical products, breath diagnostics to industrial controls to automotive gas sensing products.

Most of the current portable digital gas detection products on the market are battery operated and use electrochemical cells for sensors, they are very expensive typically $500 to $1000, require frequent calibration to maintain accuracy because of sensor drift, and frequent sensor and battery replacements, other products use Metal Oxide Semiconductor sensors which take very large amounts of power and therefore can not be operated for a reasonable time of 1 year or even 1 month on small batteries such as a 9 volt battery. Therefore there is a need for a low cost, reliable, low power, accurate, easy to use battery powered unit to detect various gases such as CO which can be self calibrating. The parameters of interest include concentration, toxicity to humans, traveling weighted averages (TWA), total dose, as well as rate of change of the of the target gas such as CO as well as rapid regeneration and reset.

Further more there is a need for a small fast responding CO detector for carrying on a person such as a beeper or a pocket model, the novel invention allows all of these advantages and has additional advantages of operating over a larger range of humidity and temperature, responding faster and providing more accuracy and more stability than any other technology.

Specifically for the case where the target gas is CO and the sensor is one or more CO optically responding sensors, such as described in U.S. Pat. No. 5,063,164 and or improvements in that technology such as those described in the U.S. Pat. Nos. 5,624,848; 5,280,273; as well as applications 60/051,038 and 80/026,534.

It has been determined that for the biomimetic sensors that 1) the forward reaction (response to co) is governed by a pseudo first order differential equation that may be simplified for most cases as described in detail below. 2) This equation or the pseudo first order equation are the ones followed under these conditions, respectively. If the air is clear of most or all of the CO, after an exposure, then the regeneration reaction is followed, it is may be represented by a third order differential equation. This equation may be simplified to a linear equation over some range similar to the procedure described for the forward reaction below. If the sign of the first derivative is positive the forward reaction governs thus the logic circuit and/or software follow the corresponding equation such as those suggested above). 3) If the sign of the first derivative is at or near zero the value of I(n) is taken as the CO concentration times a constant which is depend on the specific sensor being monitored and it value of either I or delta I, e.g., a series of CO sensors as described below. If the sign of dI/dt is negative the regeneration equation or look up table is followed as described in detail below. On the other hand we can be fit to a given equation such as an exponential which may be simplified by such approximation as the Taylor series. This Taylor series method is the subject of a copending application This description uses a set of sensors for the example of CO as the target gas at least two sensor of different sensitivity are used. To measure digital CO information from any set of optical responding sensing materials a more complex software is needed. The basic digital method is to fit an equation to the empirical response data of the sensor (simplify as necessary ) and then use a look up table or an algorithm for the response curve and the regeneration curves, respectively. If the forward reaction rate and reverse reaction rate are different (as they usually are different) separate equations are used. To better illustrate the invention a series of figures will be described.

Figure 1:
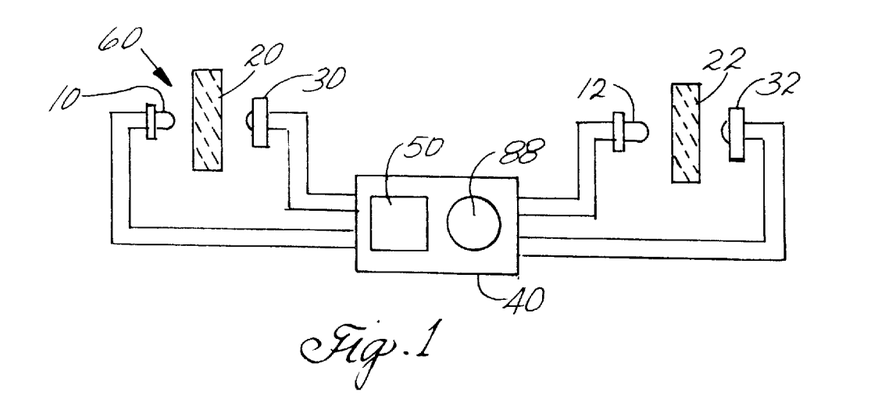
FIG. 1 is a schematic diagram of a target gas detection system embodiment of this invention designed to meet BSI CO standard that comprises two sensors.

FIG. 1 illustrates an example embodiment of a target gas detection system 60, constructed according to the practice of this invention, comprising multiple sensors. The system 60 comprises a first sensor 20 and a second sensor 22 that are prepared in the manner described above to provide desired changes in optical properties upon exposure to determined levels of a target gas, e.g., CO. The sensors are each mounted in an assembly such that a first surface of each sensor is positioned adjacent respective LEDs 10 and 12, and that an opposite surface of each sensor is positioned adjacent respective photodiodes 30 and 32. Signals sent to and from the LEDs and photodiodes are directed to a circuit 40 via suitable conductors, which circuit includes a microprocessor 50 and an alarm.

Photons are generated by the LED 10, are pulsed towards the first sensor 20, pass through the first sensor 20, and are received and measured by the photodiode 30. The target gas (CO) in the environment surrounding the first sensor reacts with the first sensor to effect a change in its photon transmission capability at a rate that is proportional to the concentration of CO in the surrounding air. The photodiode measures level of photons passed through the first sensor and passes a signal to the microprocessor 40, which is configured to determines the concentration of the target gas (CO) therefrom and activate the alarm if the CO level exceeds a preset, e.g., hazardous, level.

The microprocessor later tests,the first sensor 20 for saturation by determining whether the level of photon transmission has fallen below some optical transparency level D. If the first sensor 20 tests saturated, the microprocessor generates a signal that activates the second sensing system, comprising the second sensor 22, LED 12 and photodiode 32, and the first sensor 20 is not longer monitored. The LED 12 pulses photons at a predetermined wavelength, e.g., at 940 nm, through the second sensor 22, and photon transmission through the second sensor is measured by the photodiode 32. If the CO level is cleared, after exposure to approximately 5000 ppm CO for approximately 15 minutes, the second sensor 22 starts to regenerate. A few minutes after the second sensor 22 begins to regenerate, and the slope is negative causing the alarm to reset.

Figure 2:
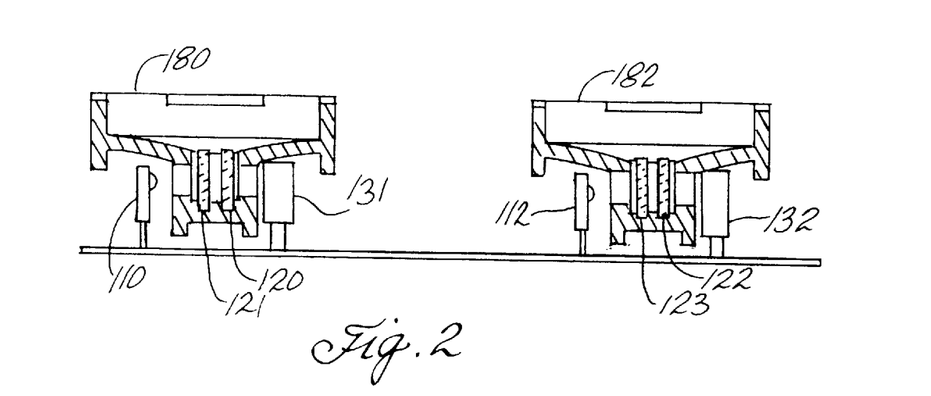
FIG. 2 is a cross-section side view of a target gas detection system embodiment of this invention comprising two sensor holders each having dual sensors disposed therein for meeting the BSI CO standard with a biomimetic sensor and generally providing rapid regeneration.

FIG. 2 illustrates another embodiment target gas detection system comprising sensor holders 180 and 182 that are each configured to physically contain or hold one or more sensors. In an example embodiment, each holder is configured to accommodate two sensors that are positioned adjacent one another. Holder 180 contains sensors 120 and 121 that are positioned adjacent one another in a stacked fashion with a determined space between adjacent sensor surfaces. A LED 110 is positioned adjacent one surface of sensor 121, and a photodiode 131 is positioned adjacent a surface of sensor 120. Likewise, holder 182 contains sensors 122 and 123 that are positioned adjacent one another in a stacked fashion with a determined space between adjacent sensor surfaces. A LED 112 is positioned adjacent one surface of sensor 123, and a photodiode 132 is positioned adjacent a surface of sensor 122.

The sensor holders 180 and 182 each include a clear windows positioned adjacent the exposed surfaces of the respective sensor pairs 120/121 and 122/123 to enable photons generated by respective LEDs 110 and 112 to pass through the respective sensor pairs 120/121 and 122/123 and be measured by respective photodiodes 130 and 132. In an example embodiment, the sensor pair 120 and 121 disposed in the first sensor holder 180 are designed to be the more sensitive target gas sensor, and the second sensor pair second pair 122 and 123 disposed in the second sensor holder 182 is designed to be the less sensitive but faster regenerating target gas sensor.

The system illustrated in FIG. 2 is controlled by the same type of control system discussed above and illustrated in FIG. 1, generally comprising a circuit that is electrically connected to each LED and photodiode to: (a) receive photon transmission level information from the photodiodes 131 and 132; and (b) send such information to a microprocessor that evaluates the level of sensor target gas exposure, activates an alarm if necessary, and switches to the second sensor system when saturation of the first sensor system is detected.

Figure 3:
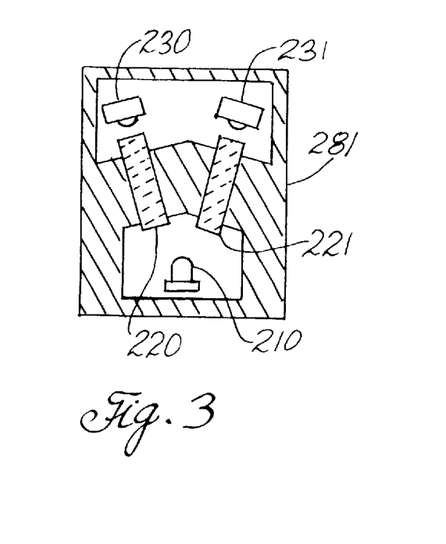
FIG. 3 is a cross-sectional top view of a target gas detection system embodiment of this invention comprising a single sensor holder having one sensor disk (such as S50s) and one disk sensor such as 5K sensor (both on edge) with one LED and two photodiodes disposed therein.

FIG. 3 illustrates another embodiment target gas detection system comprising a single sensor housing or holder 281 that is configured to accommodate placement of two sensors therein. Specifically, the holder 281 is adapted to contain a first sensor 220, that is designed to provide a high level of target gas sensitivity, and a second sensor 221, that is designed to provide a lower level of target gas sensitivity. The sensors 220 and 221 are disk shaped and are positioned in the holder in such manner as to enable a single LED 210 to pass photons through both sensors. Two photodiodes 230 and 231 are also mounted in the holder 281 adjacent ends of the sensors opposite from the LED 210 for receiving and monitoring the level of photon transmission through each respective sensor 220 and 221. In this embodiment, the and der to pass photons from one LED 210 through the edge of the sensors to the photodiodes 230 and 231, respectively.

The system illustrated in FIG. 3 is controlled by the same type of control system discussed above and illustrated in FIG. 1, generally comprising a circuit that is electrically connected to the LED and each photodiode to: (a) receive photon transmission level information from the photodiodes 230 and 231; and (b) send such information to a microprocessor that evaluates the level of sensor target gas exposure, activates an alarm if necessary, and switches to the second sensor system when saturation of the first sensor system is detected.

Figure 4:
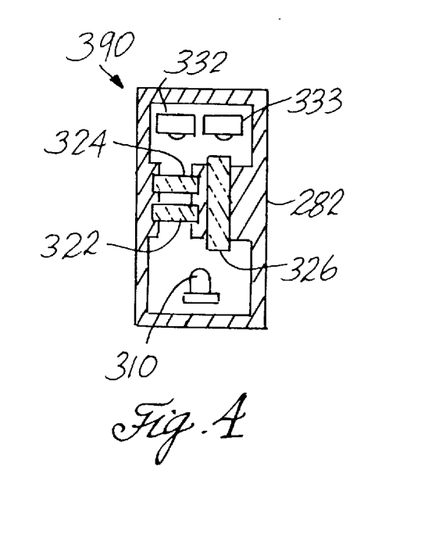
FIG. 4 is a cross-sectional top view of a target gas detection system embodiment of this invention comprising two stacked sensor disks (such as the S5Od) and another single disk sensor (such as the 5K) with one LED and two photodiodes disposed therein.

FIG. 4 illustrates another embodiment target gas detection system 390 comprising a housing 282 that is adapted to hold a series of two sensors 322 and 324, and another single sensor 326. A single LED 310 is positioned within the housing 282 so that it generates photons that are directed to both the series sensors 322 and 324, and the single sensor 326. Two photodiodes 332 and 333 are mounted in an opposite region of the housing than the LED to receive and monitor photons that are passed through respective stacked sensors 322 and 324, and the single sensor 326. In this embodiment, the stacked sensors 322 and 324 are designed to be the sensors in the system that are more sensitive to the target gas, and the single sensor 326 is designed to be the sensor the is least sensitive and faster generating. Sensor 326 can either be placed edge or face on. The edge on configuration is shown for sensor 326, while the face view is illustrated for sensors 322 and 324. The system 390 is controlled in the same manner as described above, i.e., once the sensor stack becomes saturated the microprocessor switches the system to sensor 326.

Figure 5:
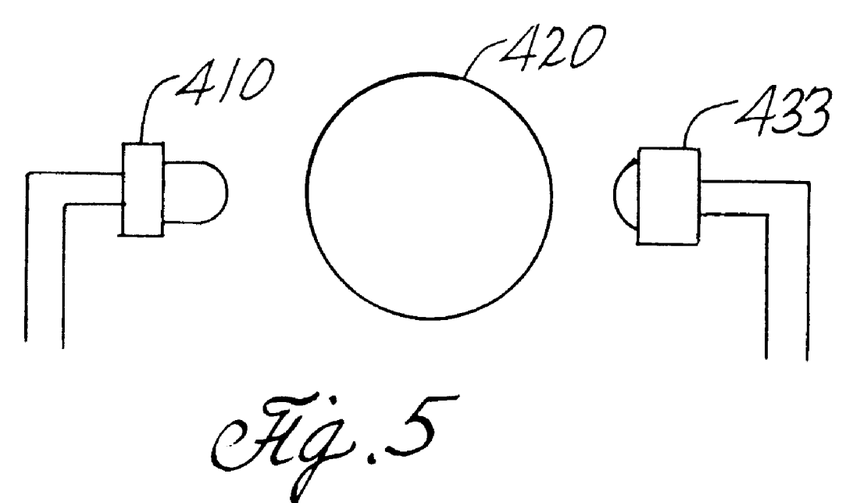
FIG. 5 is a schematic diagram of edge view optical system as used with target gas detection systems of this invention.

FIG. 5 illustrates a target gas detection system comprising a sensor 420 that is positioned in an edge view configuration for purposes of reference and clarity. The sensor 420 is positioned between a LED 410 and a photodiode 433 such that photons generated by the LED are directed toward and pass through the edge of the sensor for measurement by the photodiode 433, and controlled by the above described circuit and microprocessor means to evaluate CO concentration active an alarm.

Figure 6:
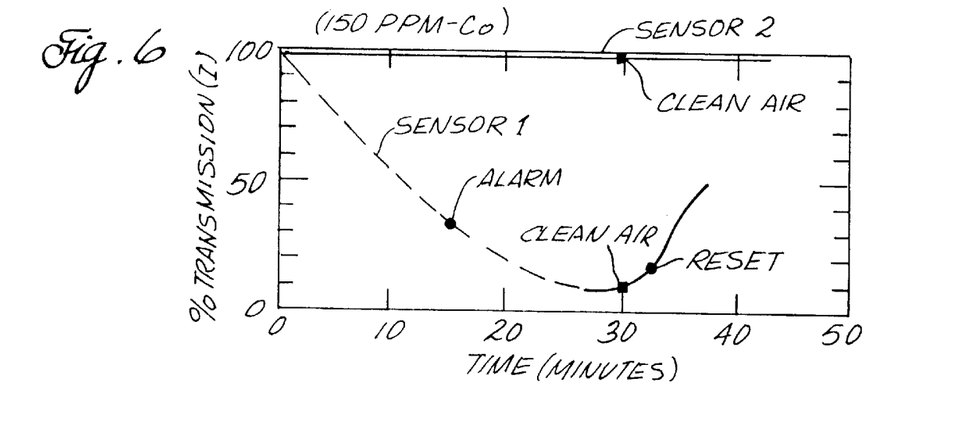
FIG. 6 graphically illustrates the response curves generated by a target gas detection system of this invention when exposed to 150 ppm CO gas.

FIG. 6 graphically illustrates response curves (percent photon transmission v. time) for a target gas detection system of this invention exposed to 150 ppm CO gas comprising two response curves; namely, a response curve for a first sensor (more sensitive to CO), and a response curve for a second sensor (less sensitive to CO). The response curve for the first sensor is illustrated as a dotted line and is shown to display a decreasing level of photon transmission percentage with time. The alarm point is indicated as occurring 15 minutes after exposure, or after the first sensor demonstrates a decrease in photon transmission of approximately 65 percent. The response curve for the first sensor also indicates a point at 30 minutes, a point of inflection, where the system is exposed to clean air and the sensor photon transmission percentage increases. A system reset occurs approximately 2 minutes after the CO level is reduced, or at 32 minutes after initial exposure. During this entire time the response curve for the second sensor is flat, indicating the CO level detected by the system did not rise above a level that saturated to the first sensor.

Figure 7:
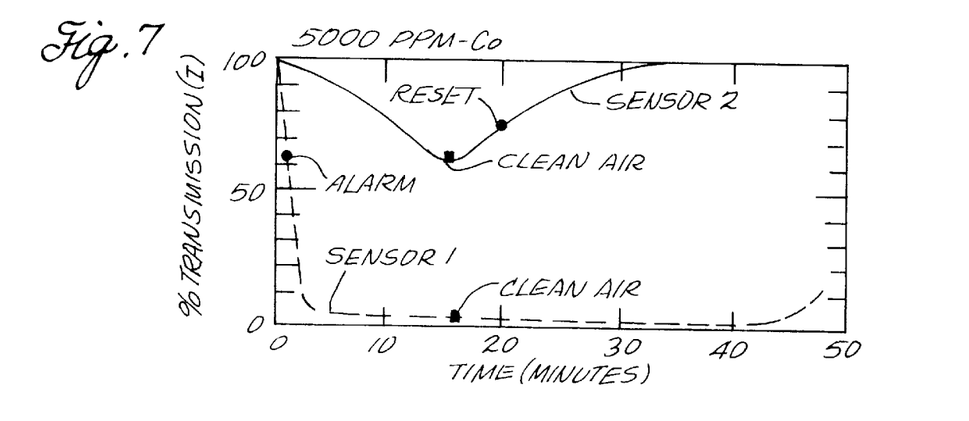
FIG. 7 graphically illustrates the response curves generated by a target gas detection system of this invention when exposed to 5,000 ppm CO gas for 15 minutes.

FIG. 7 graphically illustrates further response curves for a target gas detection system of this invention when exposed to a 5000 ppm CO gas level. Here, the response curve for the first sensor (broken line) shows that the percent photon transmission decreases at a more rapid rate than that illustrated in FIG. 1, to a point of saturation within approximately 5 minutes. The response curve for the second sensor indicates its activation by the system and illustrates a less rapid decrease in photon transmission percentage than that of the first sensor. The response curve for the second sensor also illustrates a rapid regeneration after exposure to clean air at approximately 15 minutes of less than approximately 5 minutes to reset.

Figure 8:
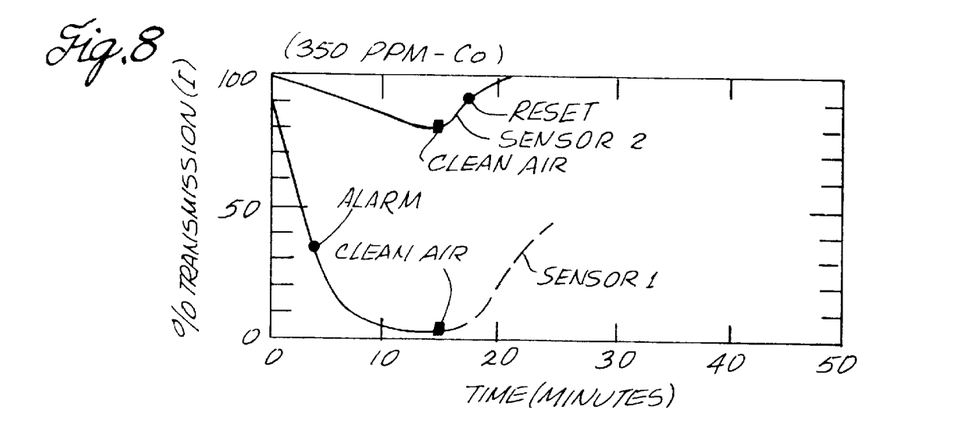
FIG. 8 graphically illustrates the response curves generated by a target gas detection system of this invention when exposed to 350 ppm CO gas for 15 minutes.

FIG. 8 graphically illustrates still further response curves for a target gas detection system of this invention when exposed to a 350 ppm CO gas level. Here, the response curve for the first sensor (broken line) shows that the percent photon transmission decreases at a more rapid rate than that illustrated in FIG. 1 (150 ppm CO), but at a slower rate than that illustrated in FIG. 3 (5,000 ppm CO), to a point of saturation within approximately 10 minutes. The response curve for the second sensor indicates its activation by the system and illustrates a less rapid decrease in photon transmission percentage than that of the first sensor, and than that of the second sensor curve illustrated in FIG. 3. The response curve for the second sensor illustrates a rapid regeneration after exposure to clean air at approximately 15 minutes of approximately 2 minutes to reset.

The correct sensitivity of each the sensors can be accomplished for almost any standard and is not limited to the BSI CO Standard. The adjusting of the chemistry, e.g., the Palladium to Copper ratio in the formulation specified in U.S. Pat. No. 5,063,164 or in a continuation-in-part application Ser. No. 08/297,141, tune the sensor response to meet a given standard.

However, a detector may also be designed to display digitally or bar graph, the levels below any specified no alarm level can be adjusted to read zero or not read. Digital display or other warnings may be permitted, even though the level of CO may be well below what the standard maker determined to be an alarm, warning or other action level(s) can be optional. There is very good reason to provide such additional features, because a major portion of the population fall in to a high risk group for CO exposure, these people include the very young, old, cardiovascular impaired, respiratory impairment, those on certain drugs, anemic people and many others which amount to about 30% of, the population, many of these people can be affected by even 2 to 4% COHb, Allred, E. N., et al, New England Jr. of Med. 321: 1426–1432 1989 and Allred, E. N. et al, Environmental Health Report et al, 91: 89"132, 199 Second, when CO is present in sufficient concentrations and for a long enough time, the sensor absorbs photons such that the light transmitted to the photodiode is reduced to a certain value delta I(n) and then levels out if the amount of CO is constant, and/or its exposure is insufficient to cause the sensor's transmission to drop below the design switch point (e.g. 30%) where the system automatically switches to the next most sensitive sensor in the series.

Depending upon the CO level to which the sensor is subjected, as well as the level of CO when placed in cleaner air, the sensor will regenerate at a variety of specific rates as it returns to toward its original state I(0) position. In this case, the alarm can be designed to silence as soon as the reversing slope is detected on a sensor whose threshold is low enough to assure safety.

In a low level alarm situation, the test button may be used to silence the alarm as the value in the alarm register is divided by four. This will turn off the alarm, but if the CO continues to be present, accumulation will continue until another alarm is reached.

Those skilled in the art would readily appreciate that the scope of the invention is not limited to the presently preferred embodiment. For example, any number of properties of the sensor may be measured such as, for example, reflection of light from the sensor. Also, one of ordinary skill in the art would recognize that any one of a variety of microprocessors and other circuit elements could be used to implement the invention, including those with built in analog to digital converters, built in liquid crystal display drivers.

One skilled in the art would appreciate an apparatus and method for digitally tracking the response of optically responding sensors for a variety of target gases. Such an apparatus and method would increase the desirability of a wide variety of products from home detectors to personnel monitors to industrial control to automotive.

Many other modifications and variations will be apparent to those skilled in the art, and it is therefore, to be understood that within the scope of the appended claims the invention may be practiced otherwise than as specifically described.

Because the current products on the market that are battery operated use electrochemical cells for sensors they are very expensive, require frequent calibration, and frequent replacement, other products use Metal Oxide Semiconductor sensors which take very large amounts of power and therefore can not be operated practically on small batteries. Therefore there is a need for a low cost, reliable, accurate, easy to use battery powered unit to detect CO level, TWA, Dose, as well as rate of change of the CO.

What is claimed is:

1. A method for detecting and determining the concentration of a target gas using a pair of optically responding sensors, the method comprising the steps of:

intermittently monitoring the optical response characteristics of a first sensor over a period of time, the first sensor having a defined target gas saturation threshold;

differentiating the monitored optical response characteristics to determine a rate of change of the monitored optical response characteristics of the first sensor;

determining the target gas concentration as a function of time of first sensor exposure;

determining whether the defined target gas saturation threshold of the first sensor is achieved;

intermittently monitoring the optical response characteristics of a second sensor over a period of time if the defined target gas saturation threshold of the first sensor has been achieved, the second sensor having a defined target gas saturation threshold that is greater than that of the first sensor;

differentiating the monitored optical response characteristics of the second sensor to determine a rate of change of the monitored optical response characteristics of the second sensor; and determining the target gas concentration as a function of time of second sensor exposure.

2. The method as recited in claim 1 wherein the optical response characteristics of the first and second sensors are monitored by passing photons through the first and second sensors and collecting the photons passed through each sensor by using a photodiode.

3. The method as recited in claim 1 further comprising the step of activating an alarm if the target gas concentration measured as a function of time of first or second sensor exposure exceeds a predetermined set point.

4. The method as recited in claim 3 further comprising the steps of:

regenerating the second sensor after the target gas concentration declines to a predetermined level; and resetting the alarm after the second sensor beings to regenerate.

5. The method as recited in claim 1 wherein the first sensor has a target gas saturation threshold of less than about 200 ppm, and wherein the second sensor has a target gas saturation threshold of greater than about 200 ppm.

6. The method as recited in claim 1 further comprising the step of assigning a sensor reading value to each monitored optical response characteristic, wherein the sensor reading is proportional to an optical characteristic of the sensor.

7. The method as recited in claim 1 wherein the target gas is carbon monoxide.

8. The method as recited in claim 1 wherein the differentiating step further comprises the steps of:

determining difference values between the first and second sensors;

storing the difference values as entries in a table of differences; and replacing entries in the table of differences as a function of new readings.

9. The method as recited in claim 8 further comprising the steps of:

summing the entries in the table of differences;

adding the summed entries in an alarm register; and entering an alarm mode when the alarm register exceeds a predefined alarm point.

10. The method as recited in claim 9 wherein the step of entering the alarm mode comprises entering one of a plurality of alarm mode levels.

11. The method as recited in claim 9 further comprising the step of increasing the rate of intermittent measurements upon entry into the alarm mode.

12. The method as recited in claim 1 wherein the optical response characteristics of the first and second sensors are monitored by directing photons to the first and second sensors and collecting the photons reflected from each sensor by using a photodiode.

13. A method for monitoring the response of a set of optically responding sensors when exposed to a target gas to determine the target gas information over a defined time period, the method comprising the steps of:

making a plurality of initial optical response readings of a first sensor system comprising a first optically-responsive sensor having a defined target gas saturation threshold;

making a plurality of subsequent optical response readings of the first optically-responsive sensor, each subsequent optical response reading being made a predetermined time after an immediately previous initial reading;

subtracting the initial readings from immediately subsequent readings to produce a plurality of differences; and using the values of the optical state of the first optically responsive sensor and a rate of change deviate to determine the gas concentration of the target gas;

switching to a second sensor system if the defined target gas saturation threshold is achieved, the second sensor system comprising a second optically-responsive sensor having a defined target gas threshold that is greater than that of the first optically-responsive sensor to extend the range of target gas concentration determination, and to facilitate rapid sensor regeneration once the target gas concentration has fallen below a predetermined level.

14. The method as recited in claim 13 wherein the target gas is carbon monoxide.

15. The method as recited in claim 13 further comprising the steps of:

summing a predetermined number of differences to produce a sum of differences; and entering an alarm mode if the sum of differences exceeds a preset value.

16. An apparatus for measuring a target gas concentration by optical technique comprising:

at least two sensor systems each comprising one or more sensors that sense the presence of a target gas by a change in optical characteristics, wherein a first sensor system includes a sensor having a target gas saturation threshold that is less than that of a sensor disposed in the second sensor system, and wherein the second sensor system sensor regenerates quicker than the first sensor system sensor when the target gas concentration is reduced to a predetermined level;

measuring means for intermittently measuring optical characteristics of at least one of the sensor systems;

means for determining magnitude of rate of change of the measured optical characteristics; and means for monitoring the target gas concentration when at least one sensor system responds to the target gas, when at least one sensor system reaches saturation, and when the least one sensor system is being regenerated.

17. The apparatus as recited in claim 16 wherein each sensor system includes a photon source and photon collector for measuring optical sensor characteristics.

18. The apparatus as recited in claim 16 wherein the measuring means comprises:

at least one photon source;

a photon detector optically coupled with each sensor and the photon source for producing a current proportional to measured optical characteristics of the optically coupled sensor;

a capacitor coupled to the photon detector, the capacitor being charged by the current; and a microprocessor coupled to the capacitor for measuring time for charge of the capacitor to reach a preset threshold, the measured time being proportional to the change in optical characteristics of the optical sensor.

19. The apparatus as recited in claim 18 wherein the optical sensor is formed from materials that undergo a change in optical characteristic when exposed to carbon monoxide.

20. A method of determining the concentration of a target gas comprising the steps of:

monitoring change in optical characteristics in a first sensor system over a period of time comprising:
a first optically-responsive sensor having a determined target gas saturation threshold;
a photon source directing photons to the first sensor; and
a photon collector for receiving photons passed from the first sensor;

determining the target gas concentration from the monitored change in optical characteristics of the first sensor system;

switching to a second sensor system in the event that the first sensor system becomes saturated to monitor the change in optical characteristic in the second sensor system over a period of time, the second sensor system comprising:
a second optically-responsive sensor having a determined target gas saturation threshold that is greater than that of the first optically-responsive sensor;
a photon source directing photons to the second sensor; and
a photon collector for receiving photons passed from the second sensor;

determining the target gas concentration from the monitored change in optical characteristics of the second sensor system;

regenerating the second sensor system when the target gas concentration drops below a predetermined level.

21. The method as recited in claim 20 wherein the first sensor has a target gas saturation threshold of less than about 200 ppm, and wherein the second sensor has a target gas saturation threshold of greater than about 200 ppm.

22. The method as recited in claim 21 wherein the second sensor has a target gas saturation threshold of greater than 5,000 ppm.

23. The method as recited in claim 20 wherein the monitored change in optical characteristics of the first and second sensor system is measured by photon transmission.

24. The method as recited in claim 20 wherein the monitored change in optical characteristics of the first and second sensor system is measured by photon reflection.

25. An apparatus for determining a target gas concentration comprising;
- more than one optically responding sensor, each sensor having a different target gas saturation threshold;
- at least one photon source for emitting photons onto the sensors;
- at least one photodetector optically coupled to receive photons from the photon source as modified by the sensors;
- means for monitoring an optical change for determining the rate of change of the optical characteristics of the sensors as a function of a plurality of measured optical characteristics; wherein the means for monitoring is switched from one sensor having a relatively low target gas saturation threshold to another sensor having a relatively higher target gas saturation threshold when the one sensor exhibits optical characteristics that are below a predetermined level.

26. The apparatus as recited in claim 25 wherein the sensors are adapted to respond to carbon monoxide.

27. The apparatus as recited in claim 25 further comprising an analog to digital converter coupled to the photodetector for determining the intensity of photons and the derivative of that intensity as a function of time.

28. The apparatus as recited in claim 25 further comprising a microprocessor comprising:
- means for assigning sensor reading values to each of the measured optical characteristics;
- means for determining differences between sensor reading values;
- memory for storing the differences;
- an alarm register for adding the sum of a plurality of the differences stored in the memory; and
- means for entering an alarm mode when value of the alarm register exceeds an alarm point.

29. A target gas detection system comprising:
- a housing comprising an opening exposed to receive surrounding air;
- a pair of optically responding sensors disposed within the housing, wherein each sensor has a target gas sensitivity that is different from the other;
- at least one light emitting diode positioned within the housing adjacent one or both sensors for generating photons onto one or both of the sensors;
- a pair of photodiodes disposed within the housing on an opposite side of a respective sensor than the light emitting diode and positioned to receive photons that are transmitted through each respective sensor;
- a microprocessor in communication with the photodiodes to measure the optical response of the sensors to a target gas, determine the target gas concentration, determine when to activate an alarm signal, and to determine when to reset the alarm signal; and
- a logic system to switch monitoring of the optical response of the sensors from a sensor that is more sensitive to the target gas to a sensor that is less sensitive to a target gas when the more sensitive sensor becomes saturated.

* * * * *